(12) United States Patent
Markey et al.

(10) Patent No.: US 9,782,325 B1
(45) Date of Patent: Oct. 10, 2017

(54) NEEDLE SYSTEMS FOR DRY NEEDLING

(71) Applicant: PHYSIO PARTNERS, LLC, Prescott, AZ (US)

(72) Inventors: Laura Markey, Prescott, AZ (US); Jeremiah Jorgensen, Lincoln, NE (US)

(73) Assignee: PHYSIO PARTNERS, LLC, Prescott, AZ (US)

( * ) Notice: Subject to any disclaimer, the term of this patent is extended or adjusted under 35 U.S.C. 154(b) by 0 days.

(21) Appl. No.: 14/739,963

(22) Filed: Jun. 15, 2015

Related U.S. Application Data

(60) Provisional application No. 62/012,157, filed on Jun. 13, 2014.

(51) Int. Cl.
*A61H 39/04* (2006.01)

(52) U.S. Cl.
CPC .................................... *A61H 39/04* (2013.01)

(58) Field of Classification Search
CPC .................................. A61N 1/05; A61N 1/056
USPC .................................................. 607/115, 116
See application file for complete search history.

(56) References Cited

U.S. PATENT DOCUMENTS

| | | | | |
|---|---|---|---|---|
| 5,271,413 A | * | 12/1993 | Dalamagas | A61B 5/0535 600/547 |
| 5,306,236 A | * | 4/1994 | Blumenfeld | A61B 5/0492 600/546 |
| 2005/0154434 A1 | * | 7/2005 | Simon | A61N 1/325 607/116 |
| 2010/0036454 A1 | * | 2/2010 | Bennett | A61N 1/36003 607/46 |

OTHER PUBLICATIONS

SEIRIN Laser L-Type Acupuncture Needles;www.seirinamerica.com; Jun. 15, 2015.

\* cited by examiner

*Primary Examiner* — Christopher D Koharski
*Assistant Examiner* — Roland Dinga

(57) ABSTRACT

A needle system for use by physical therapist in intramuscular stimulation procedures. A cylindrical non-conducting grip is located at a needle second end of a linear needle. A needle first end is pointed. An electrical connecting node is located on a needle between the needle first end and the needle second end. A second grip may be disposed on the needle such that the electrical connecting node is positioned in between the first and second grips. The electrical connecting node is operatively connected to the needle. A device generating electrical impulses is operatively connected to the electrical connecting node.

8 Claims, 4 Drawing Sheets

NEEDLE SYSTEMS FOR DRY NEEDLING

CROSS REFERENCE

This application claims priority to U.S. Provisional Patent Application No. 62/012,157, filed Jun. 13, 2014, the specification(s) of which is/are incorporated herein in their entirety by reference.

FIELD OF THE INVENTION

The present invention relates to needle systems, in particular, to needle systems for intramuscular stimulation.

BACKGROUND OF THE INVENTION

Dry needling, also known as intramuscular stimulation (IMS), is a procedure used by physical therapists. In dry needling, a needle is inserted through the skin and muscle at trigger points of muscle contraction knots. In addition, dry needling may utilize a hypodermic needle as well as a filiform needle.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention a needle system for use by physical therapists in a dry needling procedure. In some embodiments, the system comprises a linear needle having a needle first end, a needle midpoint, a needle second end, and a needle body; a cylindrical non-conducting first grip having a grip first end and a grip second end; and an electrical connecting node disposed on the needle body between the needle first end and the needle second end.

Embodiments of the present invention features the first grip located on the needle near or at the needle second end. A second grip may be disposed on the needle such that the electrical connecting node is positioned in between the first and second grips.

In some embodiments, the electrical connecting node may be operatively connected to the needle. A device generating electrical impulses maybe operatively connected to the electrical connecting node for delivering electrical impulses through the needle and into nerves, motor points and trigger points in muscle tissue.

BRIEF DESCRIPTION OF THE DRAWINGS

In FIG. 6A, the prior art needle is inside a container that has a removable tab. FIG. 6B shows the prior art needle of FIG. 6A separate from the container and the tab.

DESCRIPTION OF PREFERRED EMBODIMENTS

Figure 1:
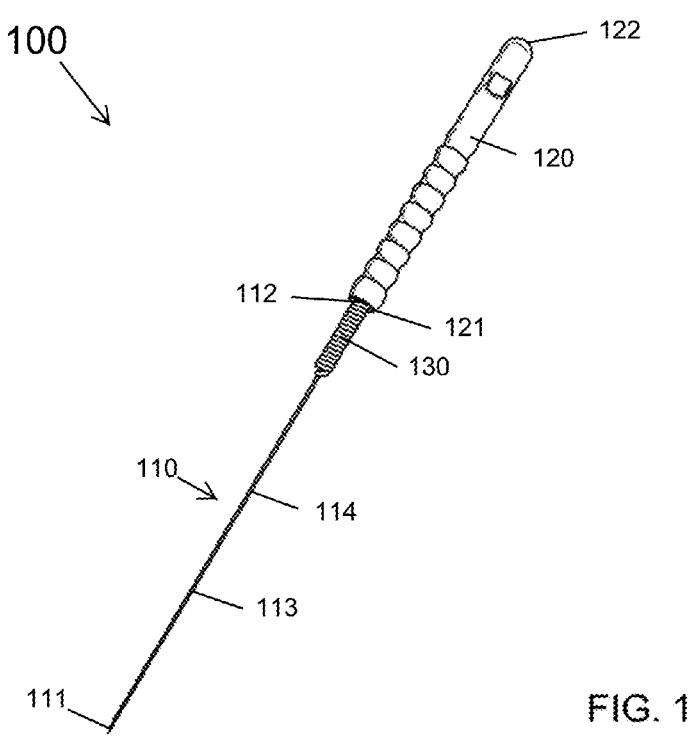
FIG. 1 shows a perspective view of an embodiment of the present invention.
Figure 2:
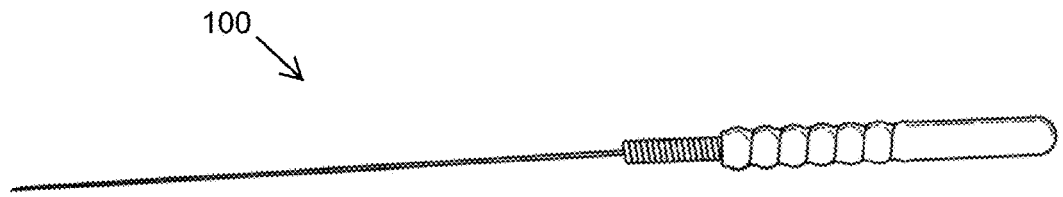
FIG. 2 shows a side view of an embodiment of the present invention.
Figure 3:
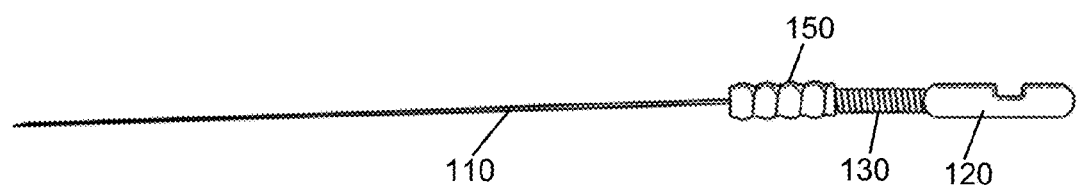
FIG. 3 shows a side view of an embodiment of the present invention.
Figure 4:
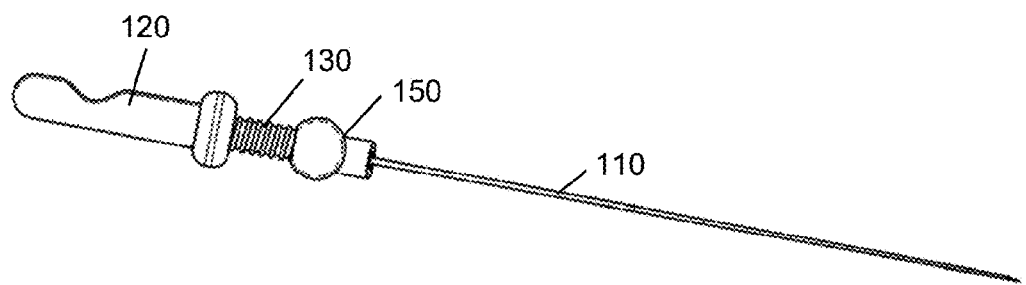
FIG. 4 shows a side view of an embodiment of the present invention.

Following is a list of elements corresponding to a particular element referred to herein:
100 Needle system
110 Needle
111 Needle first end
112 Needle second end
113 Needle body
114 Needle midpoint
120 First grip
121 First grip first end
122 First grip second end
130 Electrical connecting node
140 Device for generating electrical impulses
150 Second grip Referring now to FIGS. 1-6, the present invention features a needle system (100) for use by physical therapists in a dry needling procedure. In some embodiments, the system (100) comprises a linear needle (110) having a needle first end (111), a needle midpoint (113), a needle second end (112), and a needle body (113); a cylindrical non-conducting first grip (120) having a grip first end (121) and a grip second end (122); and an electrical connecting node (130) disposed on the needle body (113) between the needle first end (111) and the needle second end (112).

In preferred embodiments, the first grip (120) may be disposed on the needle second end (112). In one embodiment, the electrical connecting node (130) is disposed on the needle body (113) adjacent to the first grip (120). A non-conducting second grip (150) may be disposed on the needle body (113) adjacent to the electrical connecting node (130) such that the electrical connecting node (130) is disposed between the first grip (120) and the second grip (150).

In another embodiment, the electrical connecting node (130) is disposed on the needle body (113) adjacent to the first grip (120) such that the electrical connecting node (130) is disposed between the first grip (120) and a needle midpoint (114) of the needle (110). An exemplary embodiment of the electrical connecting node (130) is a conducting coil or spring.

In some embodiments, the electrical connecting node (130) is operatively connected to the needle (110). A device (140) that generates electrical impulses may be operatively connected to the electrical connecting node (130). For example, when the needle (110) is inserted through a skin and into a muscle tissue, the device (140) delivers electrical impulses through the needle (110) and into trigger points of the muscle tissue via the electrical connecting node (130).

In one embodiment, the first grip (120) is entirely disposed on the needle (110) such that the grip first end in disposed on the needle body (113) and the grip second end (122) is flushed with the needle second end (112). In another embodiment, a portion of the first grip (120) is disposed on the needle (110) and the grip second end (122) extends past the needle second end (112).

In some embodiments, the needle (110) may be solid or hollow. In other embodiments, the needle (110) is a hypodermic needle or a filiform needle. In still other embodiments, the needle first end (111) is pointed, conically pointed, or angularly slanted.

In some embodiments, the first grip (120) may comprise a smooth surface, a textured surface, or a combination thereof. Preferably, the textured surface provides for a non-slip grip to a user. The textured surface may comprise bumps, nubs, ridges, or combinations thereof. In other embodiments, the first grip (120) may comprise an open grip first end (121) and a closed grip second end (122). Alternatively, the first grip (120) may comprise an open grip first end (121) and an open grip second end (122).

In some embodiments, the second grip (150) may comprise a smooth surface, a textured surface, or a combination thereof. Preferably, the textured surface provides for a non-slip grip to a user. The textured surface may comprise bumps, nubs, ridges, or combinations thereof. The second grip may have a through-channel disposed from a second grip first end to a second grip second end. A portion of the needle body may be disposed through the through-channel. In other embodiments, the second grip is elongated, spherical or cylindrical in shape. In still other embodiments, the first grip (120) and the second grip (150) may have the same length. Alternatively, the first grip (120) may be relatively longer than the second grip (150).

In some embodiments, the needle (110) has a standardized length. In some embodiments, the needle (110) is less than 100 millimeter (mm) in length. In other embodiments, the needle (110) is between 20 to 40 mm in length, between 40 to 60 mm in length, between 60 to 80 mm in length, or between 80 to 100 mm. In still other embodiments, the needle (110) is greater than 100 mm in length.

In some embodiments, the needle (110) has a standardized diameter. In one embodiment, the standardized diameter is less than 1 mm in diameter. In another embodiment, the needle (110) is less than 0.5 mm in diameter. For example, the needle (110) is between about 0.1 and 0.2 mm in diameter. As another example, the needle (110) is between about 0.15 and 0.25 mm in diameter, between about 0.25 and 0.35 mm in diameter, or between about 0.35 and 0.45 mm in diameter.

In some embodiments, the grip first end (121) is positioned at a standardized distance from the needle first end (111). In some embodiments, the standardized distance is less than 100 mm. In other embodiments, the standardized distance is between 20 to 40 mm, between 40 to 60 mm, between 60 to 80 mm, or between 80 to 100 mm. In still other embodiments, the standardized distance is greater than 100 mm.

In some embodiments, the needle (110) can vary in diameter from 0.20 millimeter to 0.50 millimeter. For example, longer needles may have a diameter of at least 0.30 millimeter. With respect to the length of the needle, the needles may be from about a 20 millimeter to a 100 millimeter in length. All diameters and length disclosed herein are for exemplary purposes only. Any appropriate diameters and length may be used in accordance with the present invention.

In some embodiments, the first grip (120) and second grip (150) may be constructed from non-conducting materials such as an elastomeric, a polymeric, or rubber material. In other embodiments, the needle (110) and the electrical connecting node (130) may be constructed from conducting materials. For example, the conducting material may be a metal such as stainless steel, gold, silver, or any other suitable metal.

The present invention is surprisingly effective for improving tactile resonance through a plastic versus handle, as opposed to a solid metal handle. The needle system has a better ease of deployment into the skin than a needle with a full metal handle. It also allows for the provision of electrical stimulation through the same needle. Moreover, the present invention provides a more uniform and effective location for the attachment site of the electrical connecting node. By placing the electrical connecting node closest to its axis of insertion, the needle maintains its position in the muscle throughout the procedure, thereby improving safety and comfort. Furthermore, the torque on the needle and the potential for bending or breaking of the needle is reduced.

Without wishing to limit the invention to any particular theory or mechanism, it is believed that one of the features that facilitates for this effectiveness is that the needle system of the present invention provides efficiency in a specific procedure that may or may not include electrical stimulation. By having one needle, it reduces cost and provides flexibility for customization of treatment with electrical stimulation through the use of one treatment tool.

Figure 5A:
FIGS. 5A and 5B show needles of prior arts.
Figure 5B:
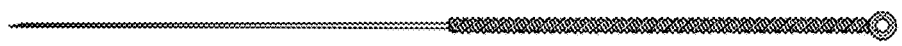
Figure 6A:
FIGS. 6A and 6B show a needle of a prior art.
Figure 6B:
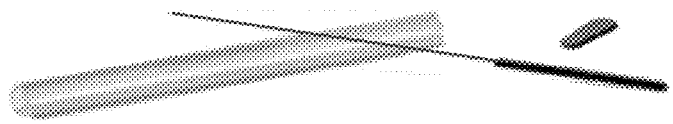

As far as the inventors are aware, the prior arts do not teach or suggest these features. As shown in FIGS. 5-6, the prior art generally teaches less versatility. For example, the prior art teaches that a plastic handle is used for non-dry needling procedures, whereas the present invention incorporates specificity and neuromuscular facilitation through the use of electricity in dry needling procedures. Moreover, the prior art does not teach a standardized length for the needle, and instead teaches that the length of the needle varies between the metal handle versus the plastic handle. Contrary to the prior art, the present invention features needles with standardized lengths.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A needle system (100) for use by physical therapists in a dry needling procedure, wherein the system (100) consists of:
   a. a linear and solid filiform needle (110) consisting of a needle first end (111), a needle midpoint (113), a needle second end (112), and a needle body (113), wherein the needle first end (111) is pointed;

b. a cylindrical, non-conducting first grip (120) consisting of a grip first end (121), a grip second end (122), and a grip length from the grip first end (121) to the grip second end (122), wherein the first grip (120) is disposed on the needle second end (112), wherein the grip length is less than half of a length from the needle first end (111) to the grip second end (122), wherein the grip second end (122) is closed off such that an interior of the first grip is inaccessible from the grip second end (122); and c. an electrical connecting node (130) disposed on the needle body (113) between the needle first end (111) and the needle second end (112), wherein the electrical connecting node (130) is fixedly attached to the needle (110) and disposed adjacent to the grip first end (121), wherein the electrical connecting node (130) is a conducting coil or spring, wherein the electrical connecting node (130) is operatively connected to the needle (110);

wherein a device (140) generating electrical impulses is operatively connected to the electrical connecting node (130), wherein when the needle (110) is inserted through a skin and into a muscle tissue, the device (140) delivers electrical impulses through the needle (110) and into trigger points of the muscle tissue.

2. The system (100) of claim 1, wherein the electrical connecting node (130) is disposed on the needle body (113) adjacent to the first grip (120), wherein the electrical connecting node (130) is disposed between the first grip (120) and a needle midpoint (114) of the needle (110).

3. The system (100) of claim 1, wherein the first grip (120) is disposed on the needle (110) such that the grip second end (122) is flushed with the needle second end (112).

4. The system (100) of claim 1, wherein a portion of the first grip (120) is disposed on the needle (110) and the grip second end (122) extends past the needle second end (112).

5. The system (100) of claim 1, wherein the needle (110) has a standardized length, wherein the grip first end (121) is positioned at a standardized distance from the needle first end (111).

6. The system (100) of claim 5, wherein the standardized length is between about 20 and 100 millimeters.

7. The system (100) of claim 5, wherein the standardized distance is between about 20 and 100 millimeters.

8. A needle system (100) for use by physical therapists in a dry needling procedure, wherein the needle system (100) consists of:

a. a linear and solid filiform needle (110) consisting of a needle first end (111), a needle midpoint (113), a needle second end (112), and a needle body (113), wherein the needle first end (111) is pointed;

b. a cylindrical, non-conducting first grip (120) consisting of a grip first end (121), a grip second end (122), and a grip length from the grip first end (121) to the grip second end (122), wherein the first grip (120) is disposed on the needle second end (112), wherein the grip length is less than half of a length from the needle first end (111) to the grip second end (122), wherein the grip second end (122) is closed off such that an interior of the first grip is inaccessible from the grip second end (122);

c. an electrical connecting node (130) disposed on the needle body (113) between the needle first end (111) and the needle second end (112) and adjacent to the first grip (120), wherein the electrical connecting node (130) is fixedly attached to the needle (110), wherein the electrical connecting node (130) is a conducting coil or spring, wherein the electrical connecting node (130) is operatively connected to the needle (110); and d. a non-conducting second grip (150) disposed on the needle body (113) adjacent to the electrical connecting node (130) such that the electrical connecting node (130) is disposed between the first grip (120) and the second grip (150);

wherein a device (140) generating electrical impulses is operatively connected to the electrical connecting node (130), wherein when the needle (110) is inserted through a skin and into a muscle tissue, the device (140) delivers electrical impulses through the needle (110) and into trigger points of the muscle tissue.

\* \* \* \* \*